(12) United States Patent
Ishihara et al.

(10) Patent No.: US 7,820,958 B2
(45) Date of Patent: Oct. 26, 2010

(54) LASER SCANNING MICROSCOPE THAT INCLUDES A SCANNING DEVICE AND AT LEAST ONE CONTROLLABLE OPTICAL ELEMENT THAT CONTROLS THE POLARIZATION PLANE OF LIGHT INCIDENT ONTO A SAMPLE, AND METHOD OF USE

(75) Inventors: Katashi Ishihara, Center Valley, PA (US); Hitoshi Hatano, Hino (JP)

(73) Assignee: Olympus Corporation, Tokyo (JP)

( * ) Notice: Subject to any disclaimer, the term of this patent is extended or adjusted under 35 U.S.C. 154(b) by 61 days.

(21) Appl. No.: 12/039,716

(22) Filed: Feb. 28, 2008

(65) Prior Publication Data

US 2008/0225906 A1 Sep. 18, 2008

(30) Foreign Application Priority Data

Mar. 12, 2007 (JP) .............................. 2007-062635

(51) Int. Cl.
*H01S 3/10* (2006.01)
(52) U.S. Cl. ....................................... 250/234; 356/318
(58) Field of Classification Search ................. 250/234; 350/364; 369/112.16–112.21; 356/318
See application file for complete search history.

(56) References Cited

U.S. PATENT DOCUMENTS 4,560,278 A * 12/1985 Shinozaki et al. ........... 356/364

| 5,614,708 | A | 3/1997 | Koishi et al. |
| 6,403,966 | B1 | 6/2002 | Oka |
| 6,639,201 | B2 | 10/2003 | Almogy et al. |
| 6,954,306 | B2 | 10/2005 | Engelhardt |
| 7,130,043 | B2 | 10/2006 | Natori |
| 7,158,294 | B2 * | 1/2007 | Motomura et al. .......... 359/385 |
| 2003/0058442 | A1 | 3/2003 | Garab et al. |
| 2005/0035281 | A1 | 2/2005 | Mehner et al. |
| 2006/0255237 | A1 | 11/2006 | Mehner et al. |

* cited by examiner

*Primary Examiner*—Seung C Sohn
(74) *Attorney, Agent, or Firm*—Arnold International; Bruce Y. Arnold

(57) ABSTRACT

An improved laser scanning microscope and method of use are disclosed that enable polarization anisotropy measurements to be made with greater sensitivity and accuracy. A controllable optical element is provided in a light path between a laser source and a sample, and is controlled so that the sample is alternately irradiated with light beams that are orthogonally polarized. This enables the signal strength to be higher than with previous laser scanning microscopes. Moreover, because the orthogonally polarized light beams that are alternately incident onto a sample may be switched at a high rate, a reduction may be achieved in the influence of molecular motion within a sample in which high speed biological reactions are observed.

26 Claims, 13 Drawing Sheets

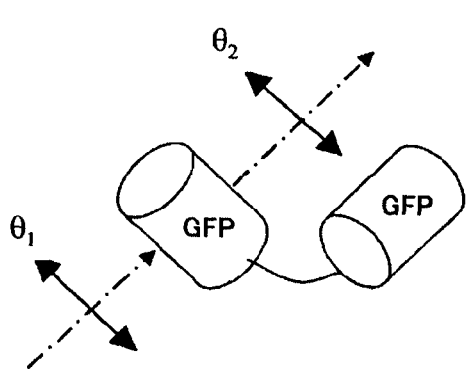 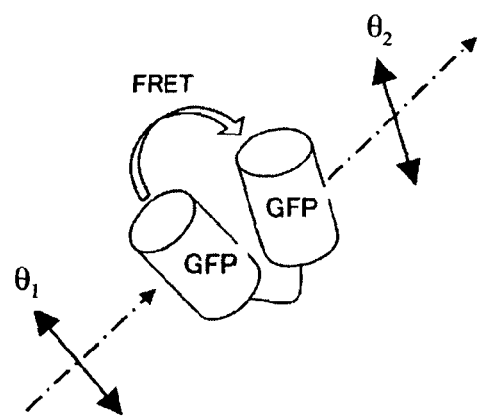
Fig. 1(a)
(Prior Art)
Fig. 1(b)
(Prior Art)

LASER SCANNING MICROSCOPE THAT INCLUDES A SCANNING DEVICE AND AT LEAST ONE CONTROLLABLE OPTICAL ELEMENT THAT CONTROLS THE POLARIZATION PLANE OF LIGHT INCIDENT ONTO A SAMPLE, AND METHOD OF USE

This application claims the benefit of foreign priority under 35 U.S.C. §119 of JP 2007-062,635 filed Mar. 12, 2007, the disclosure of which is hereby incorporated by reference.

BACKGROUND OF THE INVENTION

Recent microscopic observation techniques target not only the form of a sample but also biological reactions in living specimens. Fluorescence observation using homo-fluorescence resonance energy transfer (hereinafter termed 'Homo-FRET') is known as one such observation technique.

Fluorescence resonance energy transfer (hereinafter 'FRET') is a phenomenon caused by two fluorescent molecules, one of which is termed a 'donor molecule' and the other of which is termed an 'acceptor molecule'. The donor molecule is excited by excitation light and it transfers excitation energy to an adjacent acceptor molecule, whereby the acceptor molecule, which was in the ground state, is excited and emits fluorescence. Some additional requirements, such as the requirement that the donor molecule and acceptor molecule be sufficiently near each other (i.e., within a range of approximately 1 to 10 nm) must be satisfied in order for FRET to occur. FRET enables the organic activity of a specimen to be observed.

For example, a reagent (such as calcium ions), which reacts with a substance closely related in organic activity, can be used to observe the organic activity of a specimen through the presence, distribution, and changes in the calcium ions, since such a reagent changes the distance between the donor and acceptor molecules.

When the donor and acceptor molecules are different types of fluorescent molecules, the FRET is termed "Hetero-FRET." On the other hand, when the donor and acceptor molecules are the same type of fluorescent molecule, the FRET is termed "Homo-FRET." "Hetero-FRET" and "Homo-FRET" differ significantly from each other with regard to the observation technique used.

In Hetero-FRET, the energy transfer occurs between fluorescent molecules having a different structure and thus the fluorescent emissions from the two types of molecules have different spectrums. Thus, in Hetero-FRET, the fluorescent wavelength of the acceptor molecules is detected instead of the fluorescent wavelength of the donor molecules. The fluorescence of the donor molecules is distinguished from the fluorescence of the acceptor molecules by being at a different wavelength. Moreover, in Hetero-FRET observations, there is also a difference in the intensity of fluorescence emitted by the two types of molecules, and thus Hetero-FRET can also examine the different fluorescent emission intensities.

In Homo-FRET, the donor molecule and the acceptor molecule are identical (i.e., they are the same type of molecule) and thus the fluorescence from each has the same identical wavelength. Thus, Homo-FRET observations that use a difference in wavelength are not possible. Instead, a polarization anisotropy is used to observe Homo-FRET observations. When a fluorescent molecule is excited by a linearly polarized excitation light, the emitted fluorescence will normally have the same linear polarization. However, if FRET occurs between the excitation and the emission of fluorescence, the polarization will be disrupted so as to result in a polarization anistropy. Thus, a Homo-FRET observation can be obtained by observing the polarization anistropy that occurs in the fluorescence that is emitted when a linearly polarized light beam is incident on the specimen.

Generally, in polarization anisotropy observations, two linearly polarized light beams, one that is polarized parallel to the linearly polarized light that is incident onto the sample, and the other that is polarized perpendicular to the linearly polarized light that is incident onto the sample, are observed and their ratio is used to determine the degree of disruption of the polarization (i.e., the degree of polarization anisotrophy). In prior art polarization anisotropy observations, a polarizing beam splitter is provided in the optical path of the fluorescence in order to separate the light for observation into two beams that are polarized in orthogonal directions.

However, a high signal-to-noise ratio (hereinafter S/N ratio) is required for Homo-FRET polarization anisotropy observations. Therefore, the prior art structure, such as the structure disclosed in The Biophysical Journal, Volume 80, pp 3000-3008, June 2001, does not allow for satisfactory observations to be obtained. Furthermore, laser scanning microscopy (hereinafter LSM) requires the detection of the polarization anisotropy with a particularly high sensitivity and accuracy.

BRIEF SUMMARY OF THE INVENTION

The objective of the present invention is to provide a laser scanning microscope having a high sensitivity and accuracy in detecting polarization anisotropy. More particularly, the present invention relates to a laser scanning microscope that is suitable for detecting polarization anisotropy caused by Homo-FRET.

BRIEF DESCRIPTION OF THE DRAWINGS

The present invention will become more fully understood from the detailed description given below and the accompanying drawings, which are given by way of illustration only and thus are not limitative of the present invention, wherein:

FIGS. 1(a) and 1(b) are illustrations for explaining the principle of disruption of polarization (i.e., of the polarization anistropy) that occurs in Homo-FRET;

DETAILED DESCRIPTION

Figure 2A:
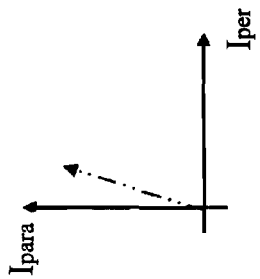
FIGS. 2(a) and 2(b) are illustrations for explaining the principle of Homo-FRET observation.
Figure 2A:
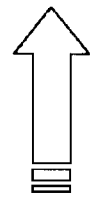
Figure 2A:
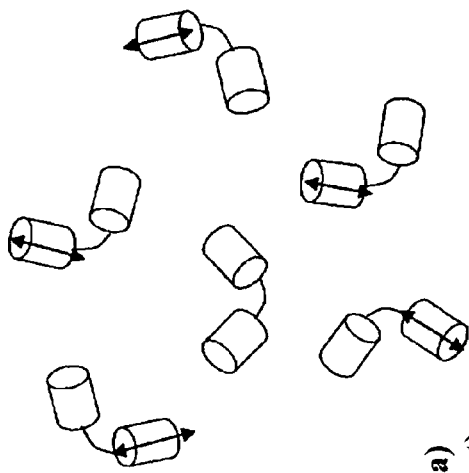
Figure 2A:
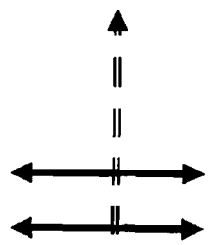

The objective of the present invention is achieved by providing a conventional laser scanning microscope with components that enable the fluorescence anisotropy of a sample irradiated with excitation light to be measured with greater sensitivity and accuracy. This is achieved by providing a conventional laser scanning microscope with a component that functions to improve the signal strength which, in turn, increases the S/N ratio of light detected by the laser scanning microscope when detecting fluorescence anisotropy of a sample.

According to the present invention, a first controllable optical element is provided that may be controlled by external signals. The first controllable optical element includes a crystal, liquid crystal or similar structure that functions to split linearly polarized light that is incident thereon into two polarization components that propagate within the structure. External signals applied to the first controllable optical element function to form a diffraction grating within the structure during periods the external signals are applied. The diffraction grating functions to diffract light of one polarization component but not to diffract light of the other polarization component. When external signals are not applied to the first controllable optical element a diffraction grating is not formed. By sequentially energizing the diffraction grating and not energizing the diffraction grating, two light beams that travel in different directions alternately emerge from the first controllable optical element in sequence, with each light beam being formed of linearly polarized light that has its polarization direction orthogonal to the polarization direction of the other emerging light beam. Thus, the first controllable optical element may be controlled to separate incident light, such as linearly polarized laser light, into two polarization components that alternately emerge from the first controllable optical element in different directions. External signals that are input to the first controllable optical element may control the proportion of polarized light components in the two beams that alternately emerge from the first controllable optical element and the rate at which the polarization of the light emerging from the first controllable optical element is switched from a first polarization to a second polarization that is orthogonal to the first polarization.

The first controllable optical element is provided in the optical path between the laser light source and the sample. The sample is irradiated with light that emerges from the first controllable optical element, with the light being alternately and sequentially polarized orthogonally. For example, the sample may be irradiated with linearly polarized light having a first polarization direction, then irradiated with linearly polarized light having a second polarization direction that is perpendicular to the first polarization direction, then irradiated with linearly polarized light having the first polarization direction, and so on. Irradiating a sample in this manner improves the S/N ratio that is obtained, as compared to prior art methods used in laser scanning microscopes.

A first fiber optic transmission medium and a second fiber optic transmission medium may be provided in the optical path between the first controllable optical element and the sample. In this case, light beams that are linearly polarized at angles that are orthogonal to each other travel through separate fiber optic transmission media.

Only a single fiber optic transmission medium may be provided in the optical path between the first controllable optical element and the sample, with the light beams that travel through the single fiber optic transmission medium being polarized orthogonal to one another. In this case, it is desirable that a second controllable optical element that performs a similar function to that of the first controllable optical element be provided. A first linearly polarized light emerging from the first controllable optical element is directed to the single fiber optic transmission medium, a second linearly polarized light emerging from the first controllable optical element is directed to the second controllable optical element, and of the polarized light emerging from the second controllable optical element, linearly polarized light having its vibration plane perpendicular to the vibration plane of first linearly polarized light is directed to the single fiber optic transmission medium.

Further, it is desirable that the first controllable optical element be an acousto-optic tunable filter. Alternatively, the first controllable optical element may be an optical switching device using holographic polymer dispersed liquid crystals (available from Crystal Research, Inc., http://www.eocyrystal.co), as described in published patent applications US 2005/00259216 A1 and US 2005/025917 A1, the disclosures of which are hereby incorporated by reference.

A laser scanning microscope method of use according to the present invention is disclosed in which a sample is irradiated with light that is alternately and sequentially polarized orthogonally, and the polarized light components of the fluorescence emitted from the sample that are perpendicular to, and parallel to, the irradiated linearly polarized lights are measured, characterized by the fact that light from the laser light source has its polarization switched to orthogonal polarization states at a rate corresponding to the rate pixels are formed using light detected by the laser scanning microscope to form display images, or at a rate corresponding to the rate that frames are formed using light detected by the laser scanning microscope. In the case where the rate of switching the polarization to orthogonal polarization states corresponds to the rate that different pixels are displayed in the images formed by the laser scanning microscope, the switching will be herein termed 'pixel-by-pixel'. In the case where the rate of switching the polarization to orthogonal polarization states corresponds to the rate that different frames are displayed in the images formed by the laser scanning microscope, the switching will be herein termed 'frame-by-frame'.

According to the present invention, irradiation of a sample with light that is alternately and sequentially polarized orthogonally provides greater capability in detecting polarization anisotropy. The present invention may thus be realized with only minor structural changes being required to prior art laser scanning microscopes.

Because the orthogonally polarized light beams (that are alternately and sequentially incident onto a sample) may be switched at a high rate, a reduction in the influence of molecular motion within a sample in which high speed biological reactions are observed may be achieved.

Polarization anisotropy (i.e., the disruption of polarization) caused by Homo-FRET will now be described with reference to FIGS. 1(a)-5 that pertain, at least in part, to the prior art.

A typical Homo-FRET observation method uses two fluorescent molecules coupled by a 'linker'. FIGS. 1(a) and 1(b) each show a linker, with green fluorescent proteins (hereinafter termed GFP) as an example of the fluorescent molecules that are coupled by linkers. A 'linker' is herein defined as a reagent that readily reacts with an internal substance to be examined and that transforms the internal substance to a different structure. As shown in FIG. 1(b), two fluorescent molecules of the same type become closer together as a result of reacting with a linker and thereby enable Homo-FRET to occur.

A difference in polarization (i.e., polarization anisotropy) arises when Homo-FRET occurs, as will now be described with reference to FIGS. 1(a) and 1(b). Fluorescent molecules have a specific absorption property, namely, they readily absorb linearly polarized light of a particular polarization angle. In FIGS. 1(a) and 1(b), the incident light is linearly polarized at an angle $\theta_1$ (as measured from a reference plane that is not illustrated) and the emerging light is linearly polarized at an angle $\theta_2$ (as measure from the same reference plane). In FIG. 1(a), two GFPs are located too far apart for Homo-FRET to occur. In this state, $\theta_1$ equals $\theta_2$. On the other hand, in FIG. 1(b), two GFPs are sufficiently close together for Homo-FRET to occur. Here, $\theta_1$ does not equal $\theta_2$. In this case, a difference between $\theta_1$ and $\theta_2$ (i.e., the polarization anisotropy) is observed when making Homo-FRET observations.

Figure 2B:
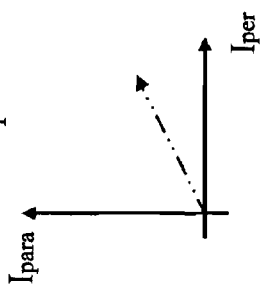
Figure 2B:
Figure 2B:
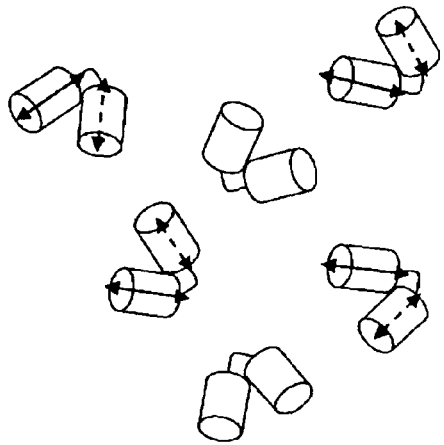
Figure 2B:
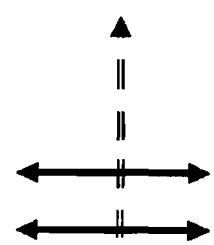

FIGS. 2(a) and 2(b) each illustrate situations wherein there are many reagents containing linkers. FIG. 2(a) is a schematic illustration showing linkers being irradiated by a linearly polarized light beam, with the pairs of fluorescent molecules being sufficiently distant from each other so that Homo-FRET does not occur. The fluorescent molecules having an absorption property that is the same as, or close to, the polarization angle of the incident linearly polarized light are excited by the linearly polarized light. In FIGS. 2(a) and 2(b), the fluorescent molecules that are excited by the incident light are marked by double-headed arrows connected by solid lines. These fluorescent molecules emit fluorescence when excited without causing Homo-FRET. The emitted fluorescence is detected as linearly polarized light having nearly the same polarization angle as the polarization angle of the incident linearly polarized light. Graph 1 (shown as an insert within FIG. 2(a)) shows the detected fluorescence when separated into the components Ipara and Iper that are parallel to, and perpendicular to, the incident linearly polarized light, respectively. In Graph 1, the linearly polarized light is transformed into fluorescence having a polarization angle that is nearly the same as the polarization angle of the incident linearly polarized light.

FIG. 2(b) is a schematic illustration showing linkers with pairs of fluorescent molecules being sufficiently close to each other to affect one another when one of the molecules is excited by being irradiated by a linearly polarized light beam. Again, the molecules having an absorbtion property that is the same as, or close to, the irradiated linearly polarized light will be excited, and the excited molecules excite the other molecule of each pair. In this case, the fluorescent molecules are not only those molecules that are excited by being directly irradiated by the linearly polarized light beam, but also include the molecules that are 'sufficiently nearby' those molecules (i.e., the 'sufficiently nearby' molecules are indicated by double-headed arrows connected by broken lines).

In this case, the fluorescent molecules emitting fluorescence include different molecules than those that are directly excited by the incident linearly polarized light beam. Therefore, the vibration plane of the linearly polarized light is not preserved in the fluorescent light that is output. Graph 2 (shown as an insert within FIG. 2(b)) illustrates the detected fluorescence when separated into the components $I_{para}$ and $I_{per}$ that are parallel to and perpendicular to the incident linearly polarized light, respectively. As is apparent from the direction of the resultant vector of these components, in Graph 2 the vibration plane of the fluorescence is at a substantially different angle than the angle of polarization of the incident polarized light, resulting in polarization anisotropy occurring.

As seen from the difference in direction of the resultant vectors when the components $I_{para}$ and $I_{per}$ that are parallel to and perpendicular to the incident linearly polarized light are combined by being added together to form a resultant vector, the amount of polarization anisotropy can be determined by comparing the parallel component $I_{para}$ to the perpendicular component $I_{per}$ of the incident linearly polarized light. The amount of polarization anisotrophy r is generally not determined by the difference in angle of the resultant vectors shown in Graphs 1 and 2, but instead is generally determined according to the following equation:

$$r = (I_{para} - I_{per})/(I_{para} + 2I_{per})$$  Equation (1)

Figure 3:
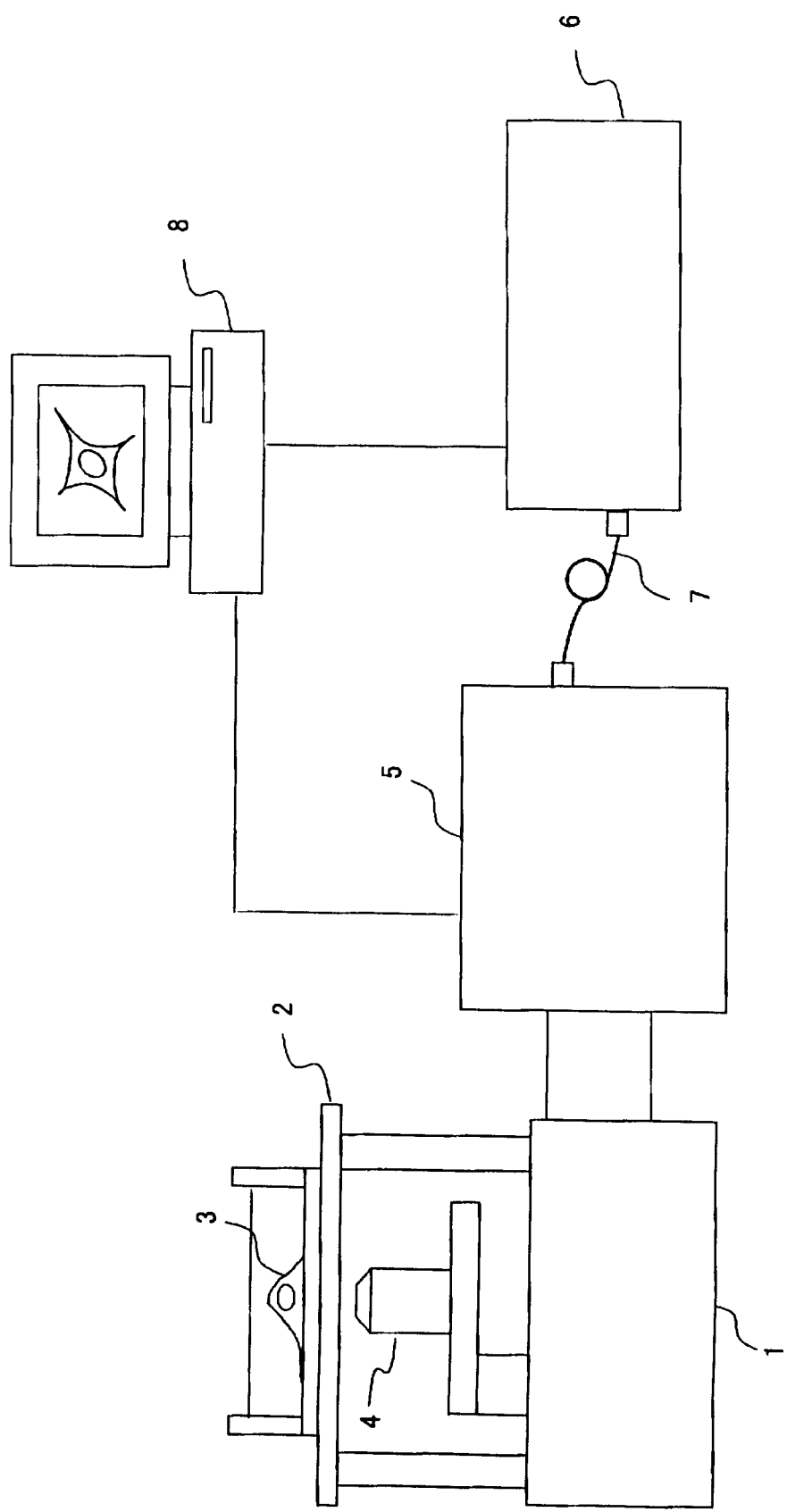
FIG. 3 is a block diagram showing the general components of a prior art laser scanning microscope.

FIG. 3 is a schematic diagram of a prior art laser scanning microscope. In this figure, a microscope body 1 has an objective lens 4 to observe a sample 3 on a stage 2. A scan unit 5 is connected to the microscope body 1. Laser light is introduced into the scan unit 5 from a laser unit 6 through a fiber optic transmission medium 7 to conduct laser scanning in the scan unit 5. For detection of the polarization anisotropy, the fiber optic transmission medium 7 is a polarization preserving optical fiber that maintains the linear polarization of the laser light that is directed to the scan unit 5. A computer terminal 8 is connected to the scan unit 5 and the laser unit 6 to control them in irradiating the sample, in detecting fluorescence from the sample, and forming images using the detected fluorescence.

Figure 4:
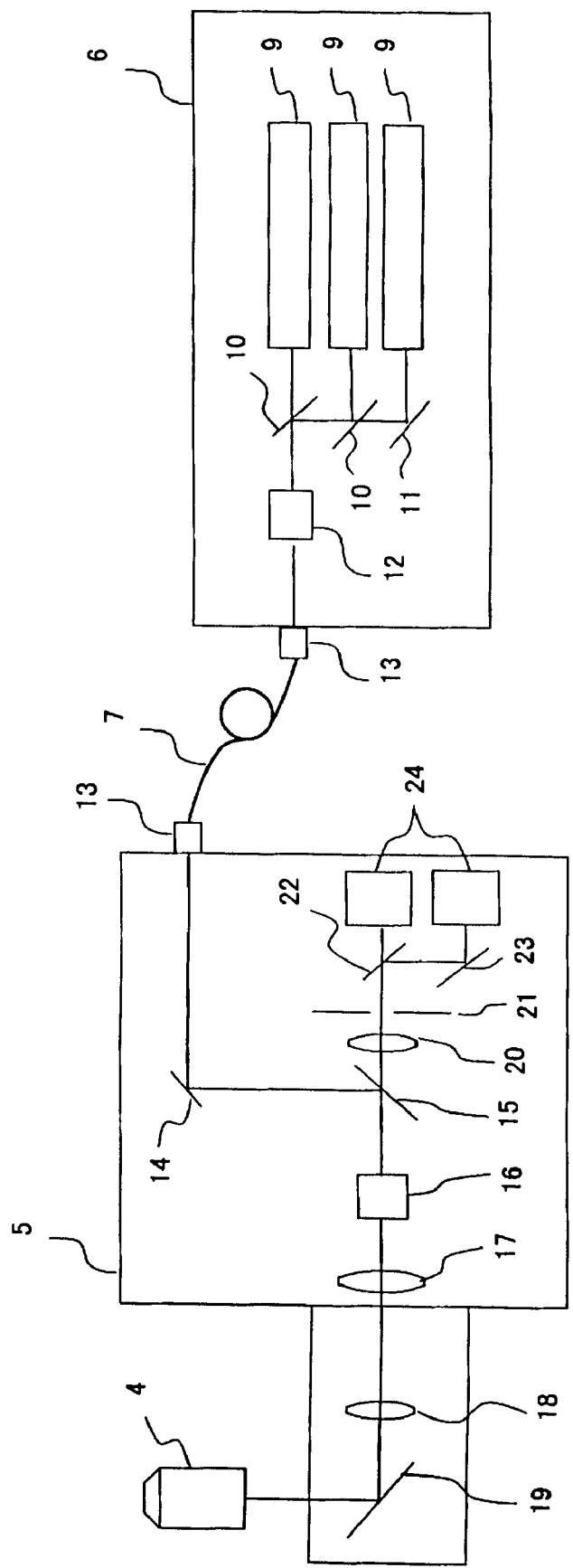
FIG. 4 is a block diagram showing the internal structure of the prior art laser scanning microscope.

FIG. 4 is a schematic diagram showing the internal structure of a prior art laser scanning microscope for polarization anisotropy observation. The prior art laser scanning microscope has multiple lasers 9, 9, 9 such as an argon ion laser (488 nm), a He—Ne green laser (543 nm), and a He—Ne laser (633 nm). A combination of dichroic mirrors 10, 10 and a mirror 11 is used to combine the optical paths of light from each laser light source to a common optical path. After being merged into a common optical path, the laser light is adjusted in the amount of light retained in the common optical path by using an acousto-optic tunable filter (hereinafter AOTF) 12. The laser light from the AOTF 12 is introduced into the fiber optic transmission medium 7 via a fiber coupling mechanism 13. As described later, the use of an AOTF allows the present invention to be realized with only minor changes to prior art laser scanning microscopes being required.

The laser light introduced into the scan unit 5 from the fiber optic transmission medium 7 is reflected to the objective lens 4 by a dichroic mirror 15 via a mirror 14. A galvanometer mirror 16, a pupil projection lens 17, an image forming lens 18, and a mirror 19 are placed in the optical path to provide a laser scanning function.

Traveling along the optical path in the reverse direction, the fluorescence from the sample is guided to the detection optical path via the dichroic mirror 15. An image forming lens 20 is placed in the detection optical path so that fluorescence emitted by an irradiated point on a sample forms an image at a confocal pinhole 21. After passing through the pinhole, the fluorescence is split into the parallel and perpendicular components $I_{para}$ and $I_{per}$ by a polarizing beam splitter 22. The split linearly polarized lights of the fluorescence are detected by two detectors 24, 24 (which may be, for example, photomultipliers). In the figure, the reference numbers 11, 14, 19, and 23 represent mirrors that fold the optical path.

Figure 5:
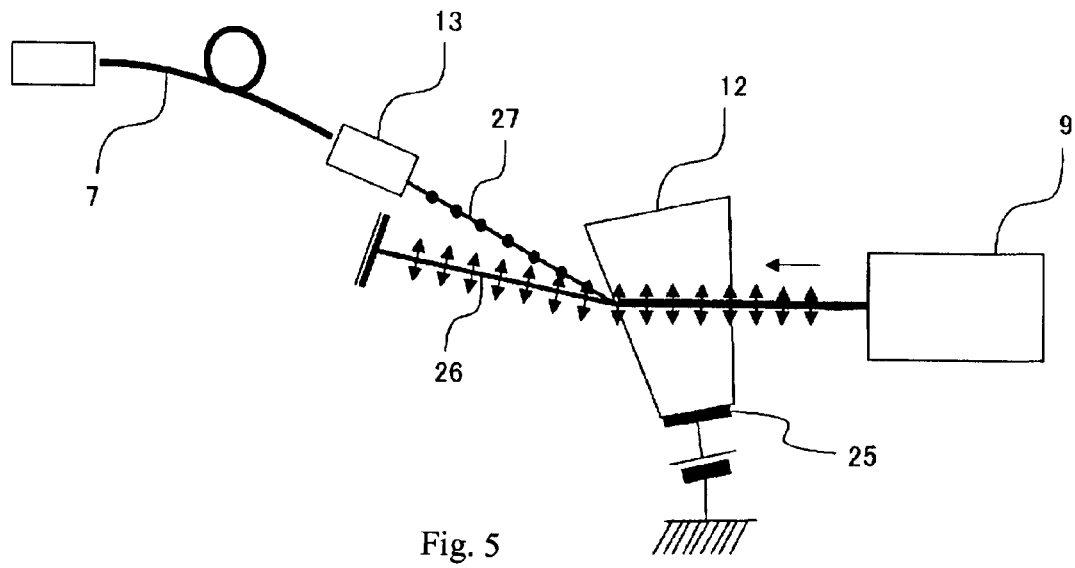
FIG. 5 is a schematic illustration for explaining the use of an acousto-optic tunable filter in the prior art laser scanning microscope.

FIG. 5 is a schematic illustration for explaining the use of an AOTF 12 in a prior art laser scanning microscope. The AOTF 12 is an optical element wherein ultrasonic waves generated by a piezoelectric transducer 25 produce standing waves that cause a diffraction grating to form in a crystalline material. The AOTF 12 (when energized) divides the incident light into a zero-order diffracted light beam and a first-order diffracted light beam. The piezoelectric transducer 25 may be further controlled to control the intensity ratio of the two beams that alternately and sequentially emerge from the AOTF.

In the prior art laser scanning microscope, the AOTF 12 (when energized) divides the incident laser light from the laser 9 into a zero-order diffracted light beam 26 and a first-order diffracted light beam 27. When the AOTF 12 is energized, only the first-order diffracted light beam 27 is directed to the sample via the fiber coupling mechanism 13. In other words, when the AOTF 12 is energized, the zero-order diffracted light beam is not used. Moreover, in the prior art laser scanning microscope, substantially no excitation light is incident onto a sample when the AOTF is not energized. Stated differently, in prior art laser scanning microscopes, the light beam that emerges from an AOTF when the AOTF is not energized is not used to irradiate a sample. The direction of propagation of the light beam that emerges from the AOTF when the AOTF is not energized is co-linear with the direction of propagation of the zero-order diffracted light beam when the AOTF is energized. The first-order diffracted light beam is a linearly polarized light beam having its plane of vibration parallel to the grating lines that are formed in the crystalline structure of the AOTF 12 when the AOTF 12 is energized.

Several embodiments of a laser scanning microscope and of laser scanning methods will now be described with reference the FIGS. 6-14(b) of the drawings that pertain exclusively to the present invention.

EMBODIMENT 1

Figure 6:
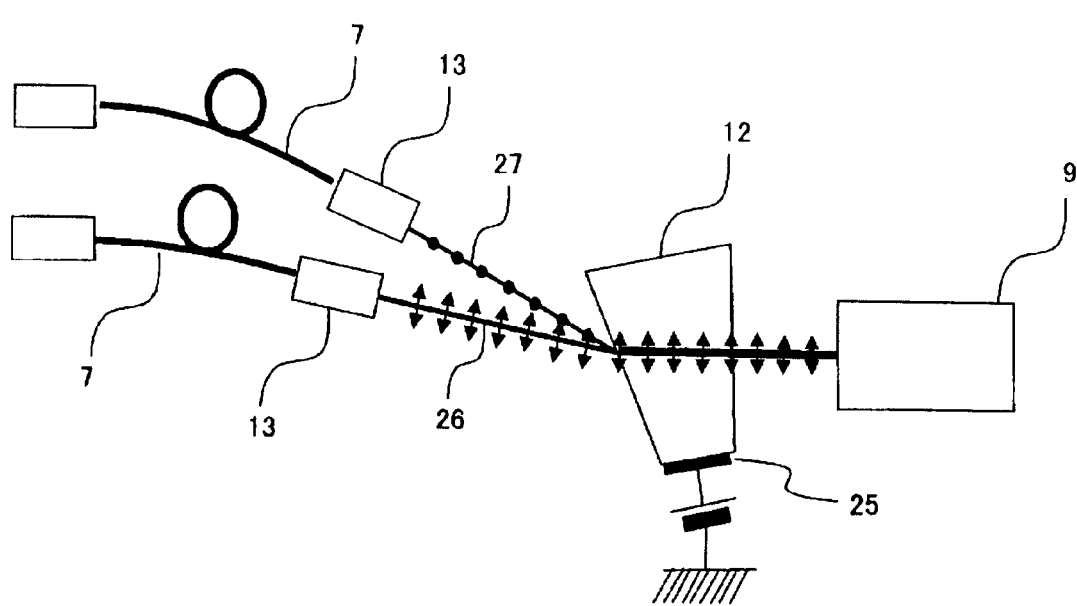
FIG. 6 is a schematic illustration for explaining the use of an acousto-optic tunable filter in Embodiment 1 of the present invention.

FIG. 6 is a schematic illustration showing a use of an AOTF 12 in the laser scanning microscope of the present invention. In the present invention, the AOTF 12 (when energized) divides the incident light from the laser 9 into a zero-order diffracted light beam (not illustrated, but that travels along same optical path as a transmitted beam 26 that emerges from the AOTF 12 when the AOTF 12 is not energized) and a first-order diffracted light beam 27. These beams are then directed to fiber coupling mechanisms 13, 13 that connect to fiber optic transmission media 7, 7 respectively. In other words, both the zero-order diffracted light beam and the transmitted beam 26 are used in the present invention, whereas they are not used in prior art laser scanning microscopes.

The transmitted light beam 26 (that emerges from the AOTF 12 when it is not energized) and the first-order diffracted light beam 27 (produced when the AOTF is energized) are linearly polarized with vibration planes perpendicular to each other. This is accomplished according to the orientation of the diffraction grating that is formed in the AOTF when the AOTF is energized. The beams that emerge from the AOTF 12 can be switched at a high rate by controlling the piezoelectric transducer 25. In prior art Homo-FRET observations using a laser scanning microscope, the polarization direction of the excitation light that is incident on a sample is not switched. Instead, the excitation light is merely turned on and off in synchronism with the detection of fluorescence on a frame-by-frame basis; therefore, the present invention enables the S/N ratio to be improved by alternately switching the direction of polarization of the excitation light that is incident onto a sample.

Instead of using an AOTF, an AOM (acousto-optic tunable modulator) or an EOHG (electro-optic holographic grating) may be used to switch the polarization direction of the excitation light that is incident onto a sample. One or more AOTFs are used as the controllable optical element to switch the polarization direction of the excitation light in the embodiments below. However, the present invention is not restricted to using a particular type of controllable optical element. An AOTF is advantageous, however, in terms of its capability of handling polarized light at multiple wavelengths.

Figure 7:
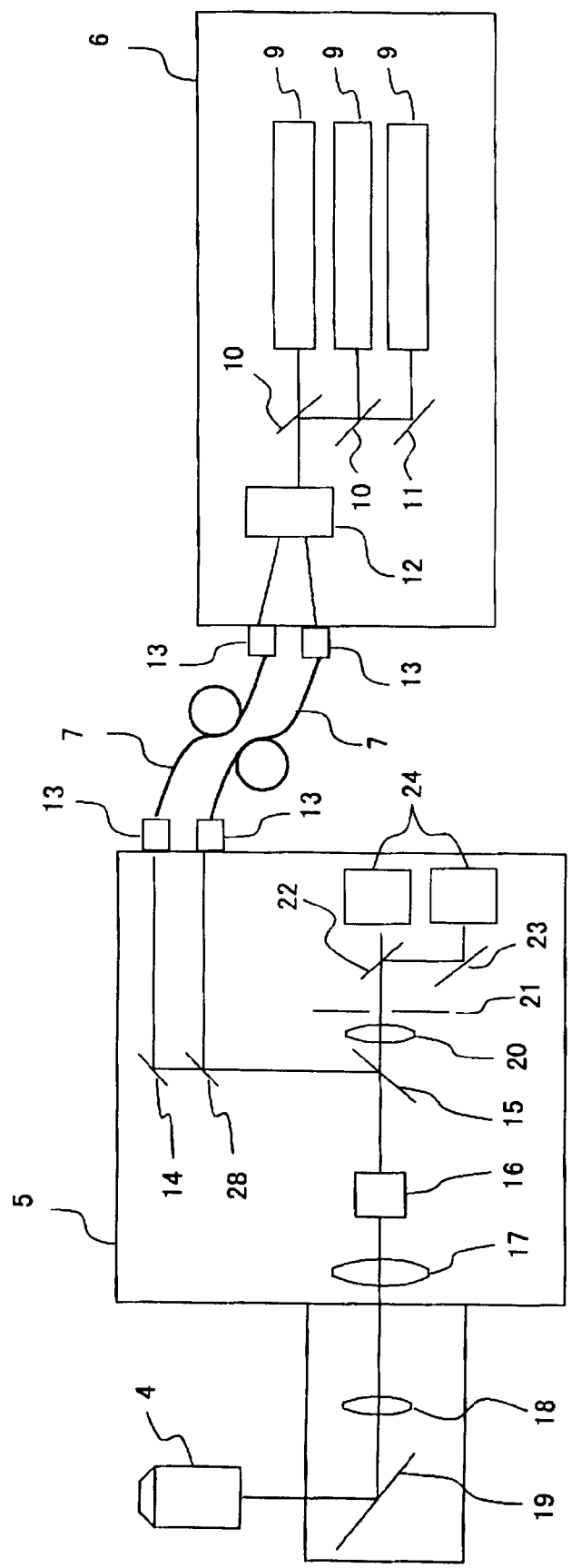
FIG. 7 is a schematic diagram showing the internal structure of the laser scanning microscope of Embodiment 1 of the present invention.

FIG. 7 is a schematic diagram showing the internal structure of a laser scanning microscope of the present invention. The laser scanning microscope of the present invention has nearly the same internal structure as the prior art laser scanning microscope shown in FIG. 4. However, the optical path from the AOTF 12 to the dichroic mirror 15 in FIG. 4 is modified. In the laser scanning microscope of the present invention, two fiber optic transmission media 7, 7 are used to introduce the transmitted light when the AOTF 12 is not energized and the first-order diffracted light when the AOTF is energized, into the scan unit 5. Then, a laser beam combining element 28 combines the two optical paths. The laser beam combining element 28 may be a half mirror or a polarizing beam splitter. The rest of the optical path is the same as that in FIG. 4 and thus further explanation will be omitted.

EMBODIMENT 2

Figure 8:
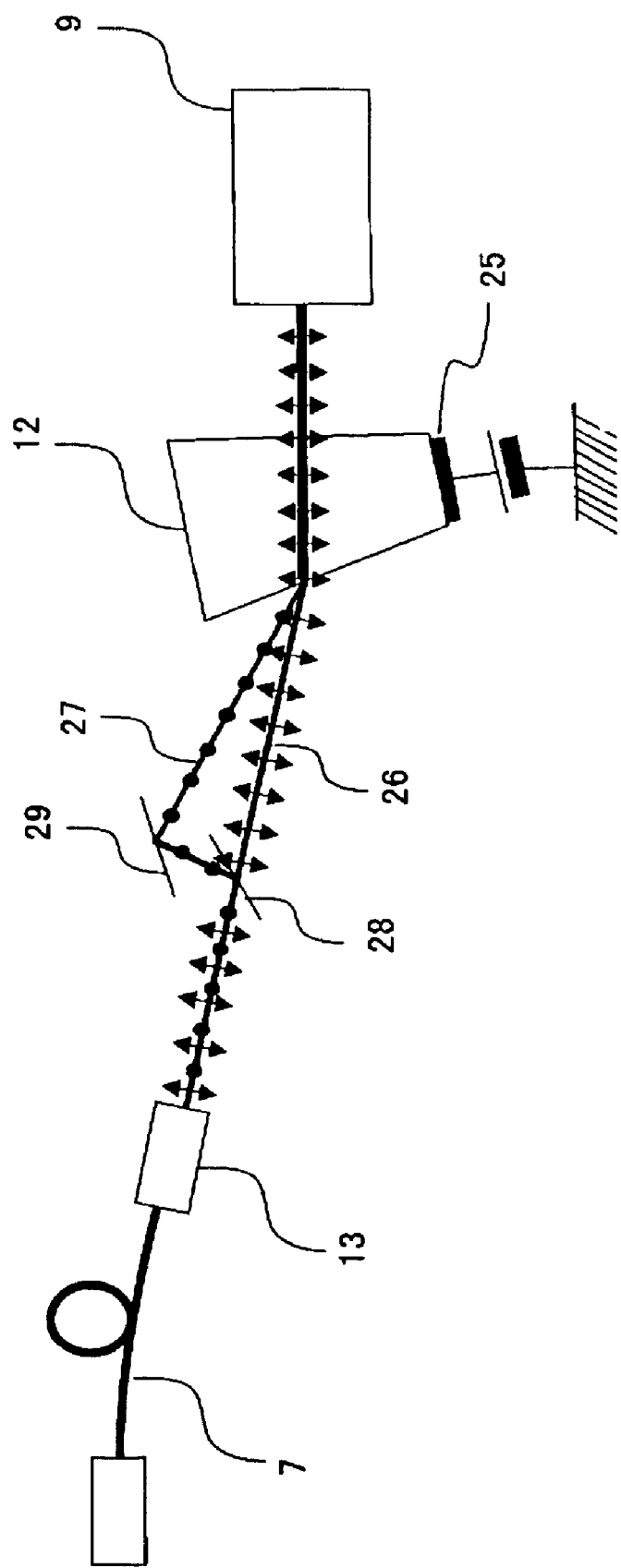
FIG. 8 is a schematic illustration for explaining the use of an acousto-optic tunable filter in Embodiment 2 of the present invention.

FIG. 8 is a schematic illustration for explaining another structure relating to the AOTF 12 in the laser scanning microscope of the present invention. In Embodiment 2, the incident light from the laser 9 is split into a transmitted light beam 26 when the AOTF is not energized and a first-order diffracted light beam 27 when the AOTF is energized, which are merged before entering the fiber coupling mechanism 13. In the embodiment shown, a combination of a half mirror 28 and a mirror 29 is used to merge these two light beams so that they travel on a common light path alternately and sequentially.

Figure 9:
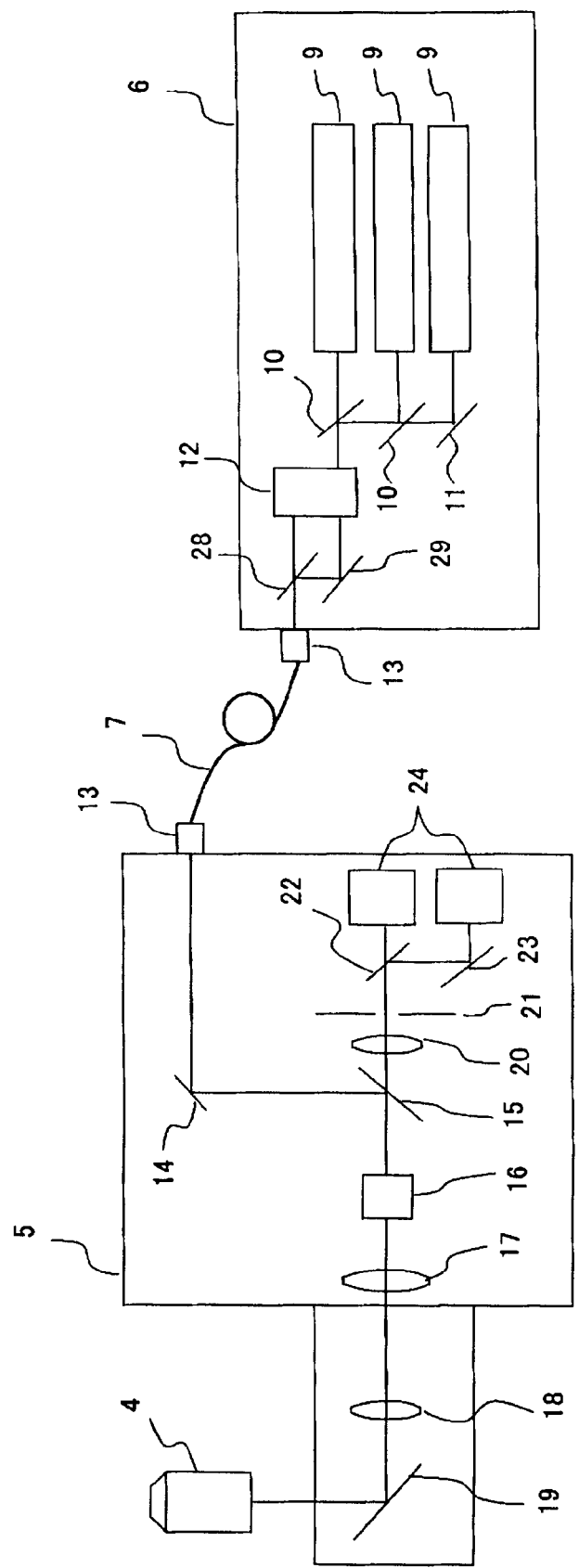
FIG. 9 is a schematic diagram showing the internal structure of the laser scanning microscope of Embodiment 2 of the present invention.

FIG. 9 is a schematic diagram showing the internal structure of a laser scanning microscope in which the structure relating to the AOTF 12 shown in FIG. 8 is incorporated. As seen from the comparison between FIGS. 9 and 4, the only difference between the two structures resides in the internal structure of the laser unit 6.

In the structure of this embodiment, lights from the lasers 9, 9, 9 are merged into one optical path by the dichroic mirrors 10, 10 and the merged laser light is directed to the AOTF 12. Upon entering the AOTF 12, the light is broken into two components by the crystalline structure of the AOTF so that it travels within the crystalline structure as two orthogonal components. Energizing the AOTF causes the light emerging from the AOTF to be diffracted. Upon emerging from the energized AOTF, most (about 94%) of the light diffracted by the AOTF is diffracted into the first order. As before, the transmitted light beam when the AOTF is not energized and the first-order light beam when the AOTF is energized are merged into one optical path by the half mirror 28 and the mirror 29, and these alternate beams are sequentially introduced into the fiber coupling mechanism 13 and the fiber optic transmission medium 7.

EMBODIMENT 3

Figure 10:
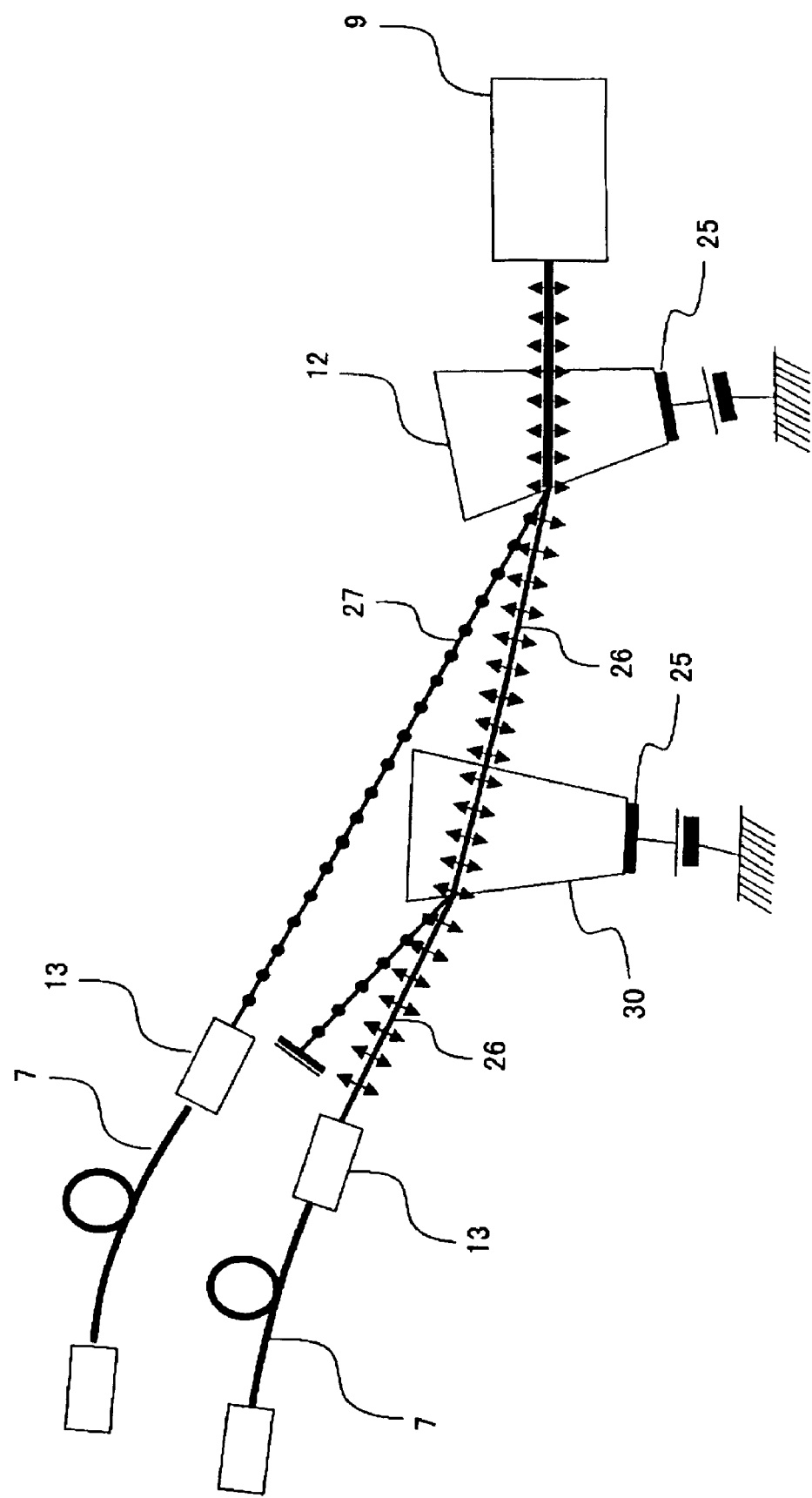
FIG. 10 is a schematic illustration for explaining the use of an acousto-optic tunable filter in Embodiment 3 of the present invention.

FIG. 10 is a schematic illustration for explaining another use of an AOTF 12 in the laser scanning microscope of the present invention. An AOTF is used to control the amount of light in the prior art laser scanning microscope. In this embodiment, it is used to control the intensity of the light and to switch the directions of the vibration planes of linearly polarized light beams that sequentially and alternately irradiate a sample.

Upon entering the AOTF 12, the light from the laser 9 is split into two components that travel within the crystalline structure of the ATOF 12. As described in earlier embodiments, by switching on and off the power to the AOTF 12, the AOTF 12 functions to split light emerging from the AOTF into a transmitted light beam that travels along the path of the zero-order diffracted beam 26 and a first-order diffracted light beam 27. Then, either one of these two light beams is introduced into a fiber coupling mechanism 13. Meanwhile, the other of these two light beams may be introduced into another AOTF 30. The light in this beam is further split into a first-order diffracted light beam (shown, but not labeled) and a transmitted light beam (that travels along a path collinear with the zero-order diffracted light beam 26) by controlling the excitation of the AOTF 30. One of these light beams is introduced into another fiber coupling mechanism 13. In FIG. 10, the light beams introduced into the another fiber coupling mechanism 13 are the zero-order light beam 26 and the transmitted light that emerge alternately from the AOTF 30 as the AOTF 30 is powered on and off. The AOTF 30 is capable not only of separating the laser light into zero-order and first-order light, but also of changing the intensity of light in these diffraction orders. In this manner, the AOTF 30 is capable of changing the intensity ratio of, for example, the first-order diffracted light and the zero-order diffracted light as well as the intensity ratio of the transmitted light and the first-order diffracted light. Thus, the present invention enables the intensities and polarization directions of light beams that sequentially and alternately irradiate a sample to be changed.

The internal structure of the laser scanning microscope of this embodiment may be obtained by simply replacing the AOTF 12 shown in FIG. 7, with the two AOTFs arranged in tandem as shown in FIG. 10. Thus, further explanation of the internal structure of the laser scanning microscope of this embodiment will be omitted.

EMBODIMENT 4

Figure 11:
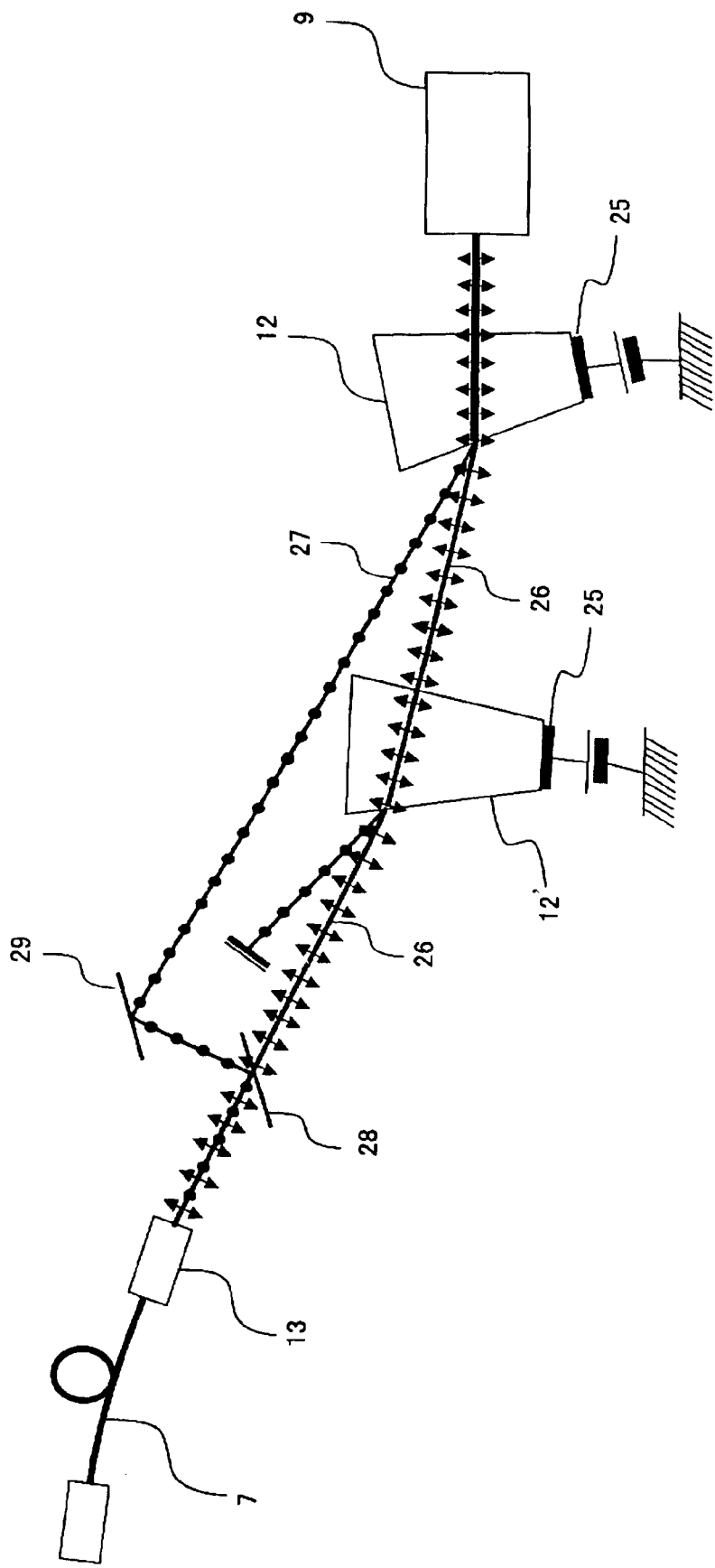
FIG. 11 is a schematic illustration for explaining the use of an acousto-optic tunable filter in Embodiment 4 of the present invention.

FIG. 11 is a schematic illustration for explaining another use of an AOTF 12 in the laser scanning microscope of the present invention. The structure of this embodiment is a combination of the structure of the AOTF in Embodiment 2 and the structure of the AOTF in Embodiment 3.

Upon entering an AOTF 12, the light from the laser 9 is split into two components by the crystalline structure of the AOTF 12, as discussed previously. Just as discussed previously, by controlling the energization of the AOTF 12, a transmitted light beam 26 (that emerges from the AOTF 12 when the AOTF 12 is not energized, and that travels along the same path as that of the zero-order beam when the AOTF is energized) and a first-order diffracted light beam 27, are made to alternately emerge from the AOTF. Then, either one of these light beams is made to enter another AOTF 12'. Just as discussed previously for the AOTF 12, by controlling the energization of the AOTF 12', a transmitted light beam 26 (that emerges from the AOTF 12' when the AOTF 12' is not energized, and that travels along the same path as that of the zero-order beam when the AOTF 12' is energized) and a first-order diffracted light beam (illustrated, but not labeled), are made to alternately emerge from the AOTF 12'. One of these light beams is not used. The remaining two linearly polarized light beams are merged by a half mirror 28 and a mirror 29 and introduced into the same fiber coupling mechanism 13. In this way, the intensity of light may be controlled and the direction of the vibration plane of the linearly polarized light incident onto a sample may be switched alternately and sequentially.

EMBODIMENT 5

Figure 12:
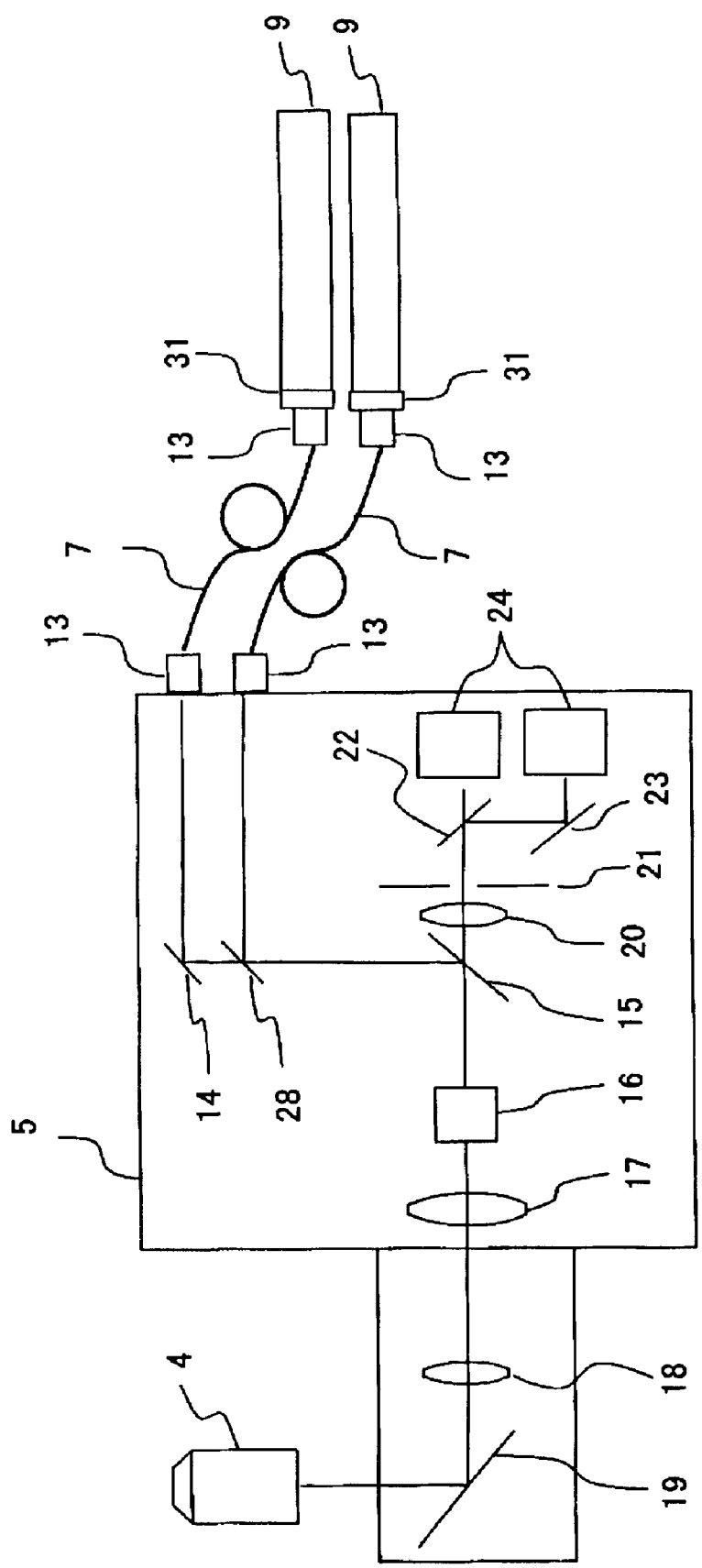
FIG. 12 is a schematic diagram showing the internal structure of the laser scanning microscope of Embodiment 5 of the present invention.

FIG. 12 is a schematic diagram showing another possible structure of a laser scanning microscope according to the present invention. The laser scanning microscope of this embodiment has nearly the same internal structure as the laser scanning microscope shown in FIG. 4. However, in the present embodiment, lights from the lasers 9, 9 having the same wavelength are introduced into the scan unit 5 using separate fiber optic transmission media 7, 7. Shutters 31, 31 are provided for selectively blocking light from the lasers. These shutters can be switched on and off at a high rate, such as frame-by-frame. The shutters 31, 31 can be mechanical shutters or nonlinear optical elements such as AOTFs and AOMs. The laser beams introduced into the scan unit 5 are polarized orthogonally, such as being linearly polarized perpendicular to each other. The two optical paths are combined by a laser beam combining element 28. The laser beam combining element may be a half mirror or a polarizing beam splitter. The remaining components in the optical path are the same as shown in FIG. 4, and thus further discussion of those components will be omitted.

Alternatively, a light beam from one laser 9 can be divided and the divided light beams can each be introduced into the scan unit 5 using two fiber optic transmission media 7, 7 instead of using two lasers.

Using a polarizing beam splitter as the beam combining element 28 of the scan unit 5 is advantageous in that laser beams having wavelengths that are identical can be merged with only a small amount of light loss. In other words, a laser scanning microscope usable not only for Homo-FRET but also for various other applications can be obtained. For example, a CW laser and a pulse laser having the same output wavelengths (or nearly the same output wavelengths) may be used in combination to achieve, in a signal laser scanning microscope, a device that enables both general microscopic observations and fluorescence lifetime imaging microscopy (termed FLIM) with no cumbersome laser switching or replacement of components.

A scanning method using the laser scanning microscope of the present invention will now be described.

Figure 13:
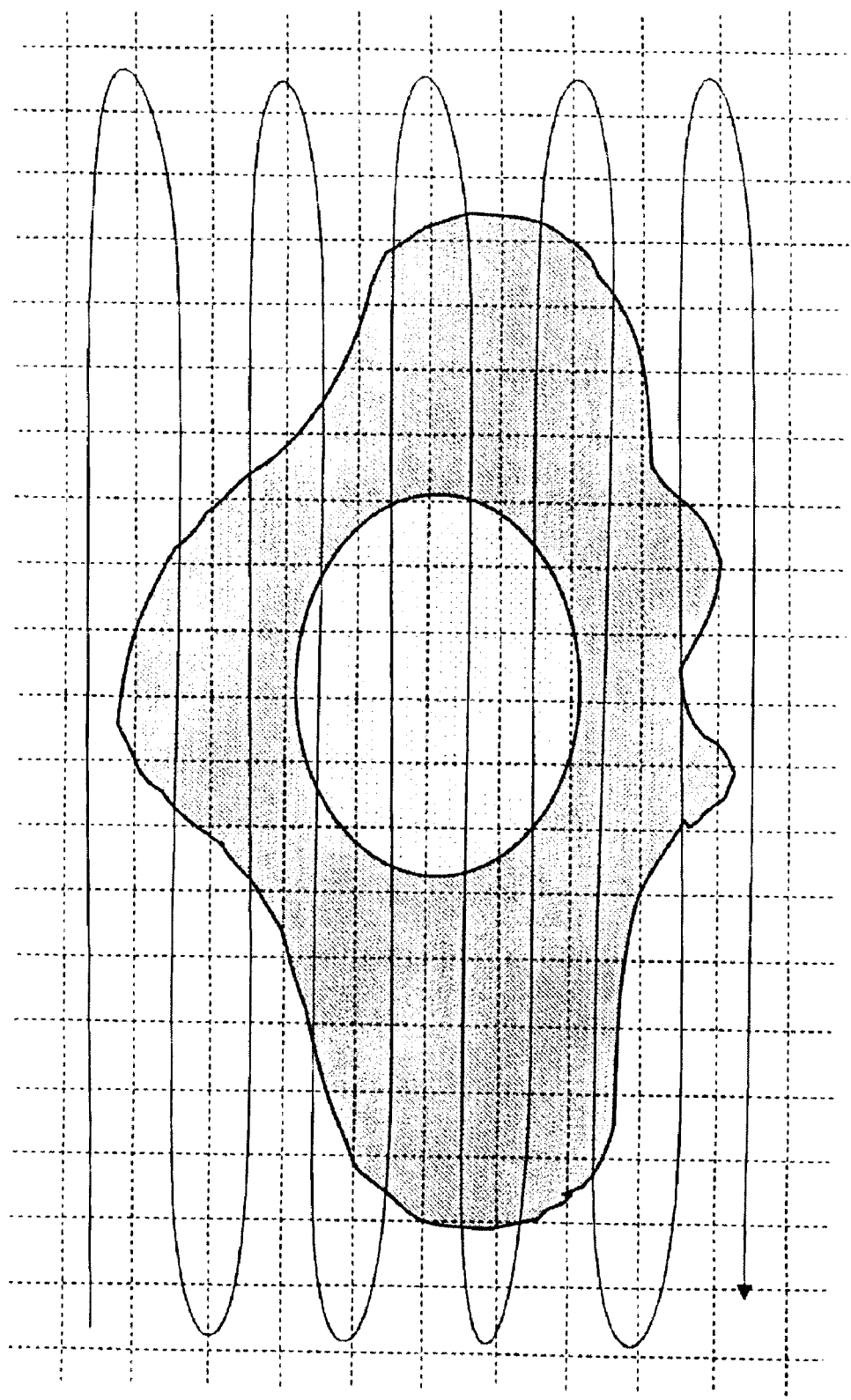
FIG. 13 is a schematic illustration showing the scanning method used in the laser scanning microscope of the present invention by way of example.

FIG. 13 is a schematic illustration showing the method of scanning the surface of a sample using the laser scanning microscope of the present invention. The sample surface is divided into a grid of pixels, the pixels are scanned by rows, and the results are combined. In an embodiment of the present invention, the perpendicular and parallel polarized light components of the fluorescence are measured while the polarization of the excitation light for exciting the sample is switched between orthogonal polarizations.

It is assumed in the explanation below that the excitation polarized lights are $I_{per}$ and $I_{para}$; the fluorescence polarized lights perpendicular to the excitation polarized lights are $I_{perper}$ and $I_{paraper}$; and the fluorescence polarized lights parallel to the excitation polarized lights are $I_{perpara}$ and $I_{parapara}$.

Figure 14B:
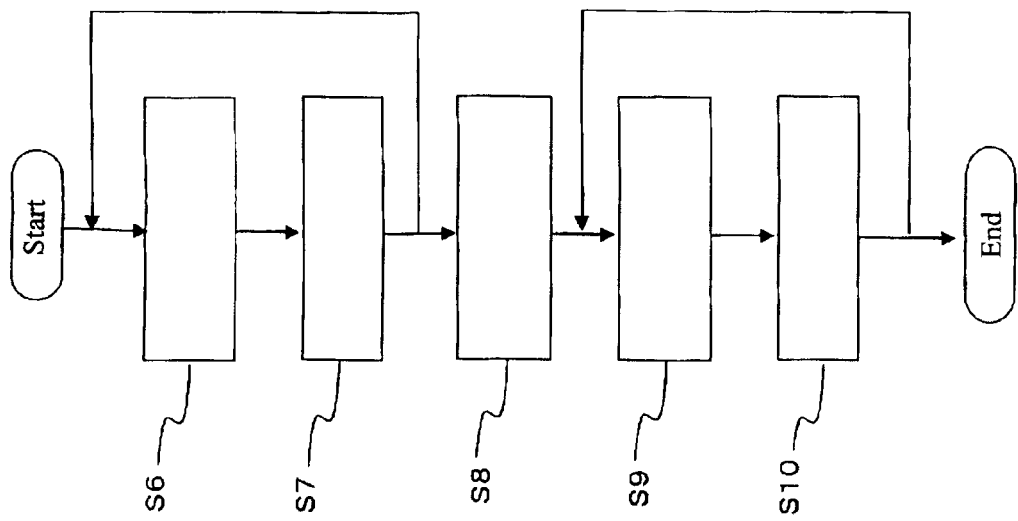
FIGS. 14(a) and 14(b) are flowcharts of the scanning methods used in the laser scanning microscope of the present invention.
Figure 14A:
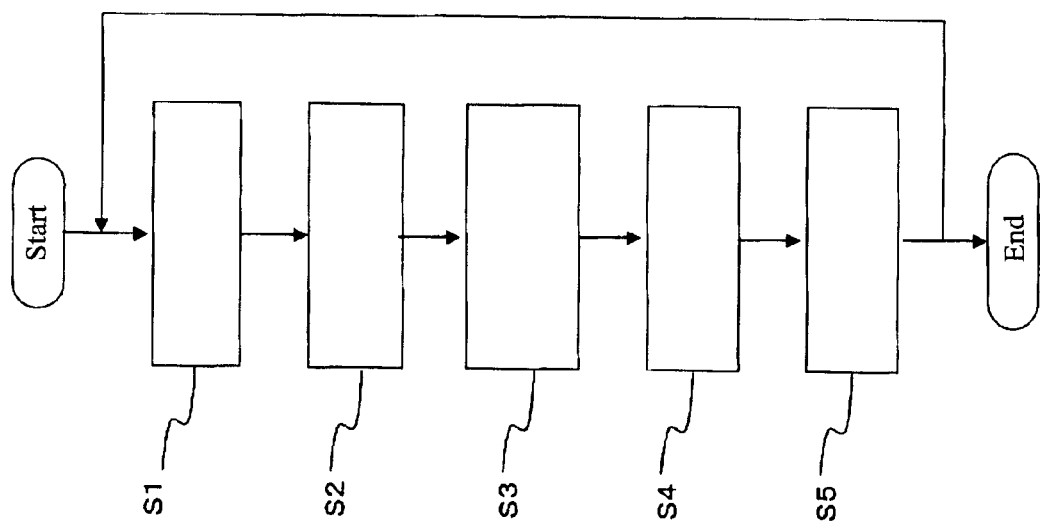

FIGS. 14(a) and 14(b) are flowcharts showing the switching of excitation polarization and the pixel scanning order, respectively, in the laser scanning microscope of the present invention.

FIG. 14(a) shows a method of switching the excitation polarization pixel-by-pixel according to the present invention. In step (S1), the perpendicular polarized light component $I_{perper}$ and the parallel polarized light component $I_{perpara}$ of the fluorescence are obtained for the first pixel. In step (S2), the excitation polarization direction is switched. In step (S3), the perpendicular component $I_{paraper}$ and the parallel component $I_{parapara}$ are detected. Thus, at this point in time, all four data points for the pixel have been detected. In step (4), the laser scan is moved to the next pixel (S4). In step (S5), direction of polarization of the excitation light is switched to restore the polarization direction to the original direction (S5). The above operation is repeated for all pixels. With this method, all pixels can be observed with accuracy. The prior art does not have a means for switching the polarization to alternate directions that are orthogonal. Moreover, the prior art does not suggest switching the polarization direction at a high rate, such as pixel-by-pixel.

FIG. 14(b) shows a method of switching the excitation polarization frame-by-frame according to the present invention. The acquisition time per frame is reduced in this embodiment compared to the flowchart in FIG. 14(a). In other words, when frames are acquired in chronological order, accurate observation is available with the time lag between frames being reduced. As used herein, the term "frame" includes all pixels of an image of a sample.

In this method, the perpendicular polarized light component $I_{perper}$ and the parallel polarized light component $I_{perpara}$ of the fluorescence are obtained for the first pixel in step (S6). In step (S7) the scan is moved to the next pixel. This operation is repeated for all pixels. In step (S7), the direction the vibration plane of the excitation light is switched. In step (S9), the perpendicular polarized light component $I_{paraper}$ and the parallel polarized light component $I_{parapara}$ of the fluorescence are obtained for the first pixel. In step (S10), the scan is moved to the next pixel. This operation is repeated for all pixels. In this way, all four data measurements are obtained for all the pixels of a frame.

As described above, a laser scanning microscope having a high capability of polarization anisotropy detection is provided.

The invention being thus described, it will be obvious that the same may be varied in many ways. For example, the orthogonal, linearly polarized light beams that travel in a single fiber optic transmission medium or in two fiber optic transmission media may instead be converted into left and right circularly polarized light beams (using known techniques) so that the light beams travel with clockwise and anticlockwise rotations. In addition, although preferably the switching of the direction of the vibration plane of the radiation incident onto the sample is performed at a rate equal to the rate of forming of pixels or the rate of forming frames of display images using light detected from the sample, other rates may be used. For example the switching rate can be faster or slower than the rate of forming pixels or frames. For this reason, the phrase "in synchronism with forming pixels or frames" is herein defined to include the situation wherein the rate of switching of the direction of the vibration plane of the incident light is equal to the rate of forming pixels or frames divided or multiplied by an integer.

Moreover, although linearly polarized light has been discussed as being incident onto the sample with the direction of the vibration plane being switched alternately, those of ordinary skill in the art would immediately recognize that the advantages conferred by the present invention do not require that the light incident on the sample be linearly polarized. Circularly polarized light can be considered to be nearly the same as linearly polarized light with the difference being its vibration plane slowly rotates as the light propagates. Thus, it would be immediately apparent to those of ordinary skill in the art that the sample could instead be repeatedly irradiated at a rapid rate using a circularly polarized light beam. For example, the sample could be irradiated very briefly by a circularly polarized light beam, followed by the sample being irradiated very briefly by the same circularly polarized beam said beam has undergone a phase delay of 90 degrees, with this process repeating at a rapid rate. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. In a laser scanning microscope that includes a scanning device and at least one controllable optical element that controls the polarization plane of light incident onto a sample, and that irradiates a sample with polarized light from a laser and detects the polarized light components of fluorescence emitted from the sample in vibration planes that are perpendicular to one another, the improvement comprising:
   providing a first controllable optical element that forms polarized light components of light incident thereon and that controls, according to external signals, light beams that emerge from said first controllable optical element, said first controllable optical element being positioned in an optical path between said laser and said sample;
wherein
   the sample is alternately irradiated with light beams that are orthogonally polarized.

2. The laser scanning microscope of claim 1, said laser scanning microscope further comprising:
   a first fiber optic transmission medium and a second fiber optic transmission medium positioned in optical paths between said controllable optical element and said sample;
wherein
   said first fiber optic transmission medium receives one of the orthogonally polarized light beams that emerge from said first controllable optical element, and
   said second fiber optic transmission medium receives the other of the orthogonally polarized light beams that emerge from said first controllable optical element.

3. The laser scanning microscope of claim 1, said laser scanning microscope further comprising:
   a fiber optic transmission medium that alternately receives said light beams that are orthogonally polarized from said first controllable optical element.

4. The laser scanning microscope of claim 2, said laser scanning microscope further comprising:
   a second controllable optical element;
wherein
   a first linearly polarized light beam that emerges from said first controllable optical element is directed to said first fiber optic transmission medium;

a second linearly polarized light beam that emerges from said first controllable optical element is directed to said second controllable optical element; and of the light beams that emerge from said second controllable optical element, a linearly polarized light beam having its plane of polarization perpendicular to said first linearly polarized light beam is directed to said second fiber optic transmission medium.

5. The laser scanning microscope of claim 3, said laser scanning microscope further comprising:

a second controllable optical element;

wherein a first linearly polarized light beam that emerges from said first controllable optical element is directed to said fiber optic transmission medium;

a second linearly polarized light beam that emerges from said first controllable optical element is directed to said second controllable optical element; and of the polarized light beams that emerge from said second controllable optical element, a linearly polarized light beam having its vibration plane orthogonal to the vibration plane of said first linearly polarized light beam is directed to said fiber optic transmission medium.

6. In a laser scanning microscope that includes a scanning device and at least one controllable optical element that controls the polarization plane of light incident onto a sample, and that irradiates a sample with polarized light from a laser and wherein light components of fluorescence emitted from the sample in specified vibration planes that are orthogonal to one another are detected, the improvement of: providing a controllable optical element that is controlled so as to alternately irradiate the sample with light beams that are orthogonally polarized.

7. The laser scanning microscope of claim 1, wherein the controllable optical element is an acousto-optic tunable filter.

8. The laser scanning microscope of claim 2, wherein the controllable optical element is an acousto-optic tunable filter.

9. The laser scanning microscope of claim 3, wherein the controllable optical element is an acousto-optic tunable filter.

10. The laser scanning microscope of claim 4, wherein the controllable optical element is an acousto-optic tunable filter.

11. The laser scanning microscope of claim 5, wherein the controllable optical element is an acousto-optic tunable filter.

12. The laser scanning microscope of claim 6, wherein the controllable optical element is an acousto-optic tunable filter.

13. The laser scanning microscope of claim 1, wherein the controllable optical element is a holographic grating.

14. The laser scanning microscope of claim 2, wherein the controllable optical element is a holographic grating.

15. The laser scanning microscope of claim 3, wherein the controllable optical element is a holographic grating.

16. The laser scanning microscope of claim 4, wherein the controllable optical element is a holographic grating.

17. The laser scanning microscope of claim 5, wherein the controllable optical element is a holographic grating.

18. The laser scanning microscope of claim 6, wherein the controllable optical element is a holographic grating.

19. A laser scanning microscope method of use, said laser scanning microscope including a scanning device and at least one controllable optical element that controls the polarization plane of light incident onto a sample, wherein a sample is irradiated with polarized light from a laser and light components of fluorescence emitted from the sample in specified vibration planes that are orthogonal to one another is detected, said method including the step of alternately irradiating the sample with light beams that are orthogonally polarized.

20. The laser scanning microscope of claim 6, wherein the controllable optical element is controlled in synchronism with forming pixels or frames of a display image of detected fluorescence emitted from the sample.

21. The laser scanning microscope of claim 1, wherein the laser scanning microscope includes an image forming lens and a pinhole aperture.

22. The laser scanning microscope of claim 21, wherein said image forming lens and said pinhole aperture are positioned so that fluorescence emitted by an irradiated point on a sample is imaged at said pinhole aperture.

23. The laser scanning microscope of claim 6, wherein the laser scanning microscope includes an image forming lens and a pinhole aperture.

24. The laser scanning microscope of claim 23, wherein said image forming lens and said pinhole aperture are positioned so that fluorescence emitted by an irradiated point on a sample is imaged at said pinhole aperture.

25. The laser scanning microscope of claim 19, wherein the laser scanning microscope includes an image forming lens and a pinhole aperture.

26. The laser scanning microscope of claim 25, wherein said image forming lens and said pinhole aperture are positioned so that fluorescence emitted by an irradiated point on a sample is imaged at said pinhole aperture.

* * * * *